(12) United States Patent
Fuller et al.

(10) Patent No.: US 10,080,874 B2
(45) Date of Patent: Sep. 25, 2018

(54) TRAP BALLOON CATHETER WITH TRAP BALLOON RETAINER

(71) Applicant: BOSTON SCIENTIFIC SCIMED, INC., Maple Grove, MN (US)

(72) Inventors: Jeffrey Steven Fuller, Brooklyn Park, MN (US); Ajay Gupta, Shoreview, MN (US); Gordon Kocur, Lino Lakes, MN (US); Patrick Boylan, Naas (IE); Fiona Byrne, Athlone (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 134 days.

(21) Appl. No.: 15/093,889

(22) Filed: Apr. 8, 2016

(65) Prior Publication Data

US 2016/0296732 A1    Oct. 13, 2016

Related U.S. Application Data

(60) Provisional application No. 62/279,983, filed on Jan. 18, 2016, provisional application No. 62/145,496, filed on Apr. 9, 2015.

(51) Int. Cl.
*A61M 25/10*    (2013.01)
*A61M 25/09*    (2006.01)
(Continued)

(52) U.S. Cl.
CPC ........ *A61M 25/10* (2013.01); *A61M 25/0169* (2013.01); *A61M 25/09* (2013.01);
(Continued)

(58) Field of Classification Search
CPC ............ A61M 2025/0008; A61M 2025/09125; A61M 2025/1081; A61M 25/0169; A61M 25/0662; A61M 25/09; A61M 25/10
See application file for complete search history.

(56) References Cited

U.S. PATENT DOCUMENTS 4,564,014 A    1/1986 Fogarty et al.
4,572,186 A    2/1986 Gould et al.
(Continued)

FOREIGN PATENT DOCUMENTS

EP    0565996 A1    10/1993
WO    9717899 A1    5/1997

*Primary Examiner* — Quynh-Nhu H Vu
(74) *Attorney, Agent, or Firm* — Seager, Tufte & Wickhem LLP

(57) ABSTRACT

Medical devices, medical device systems, and methods for using the same are disclosed. An example medical device system may include a guide catheter having a proximal end, a distal end, and a lumen extending therebetween. The guide catheter may be designed to guide a therapeutic catheter to a target site. A guidewire may be disposed within the lumen of the guide catheter. The system may also include a trap balloon catheter including a catheter shaft and a balloon coupled to the catheter shaft. The trap balloon catheter may be designed to extend through the lumen of the guide catheter to a position adjacent to the distal end of the guide catheter. A trap balloon retainer may be coupled to the catheter shaft. The trap balloon retainer may be designed to prevent a distal end of the trap balloon catheter from extending distally beyond the distal end of the guide catheter.

20 Claims, 15 Drawing Sheets

(51) Int. Cl.
   *A61M 25/01* (2006.01)
   *A61M 25/06* (2006.01)
   *A61M 25/00* (2006.01)

(52) U.S. Cl.
   CPC . *A61M 25/0662* (2013.01); *A61M 2025/0008* (2013.01); *A61M 2025/09125* (2013.01); *A61M 2025/1081* (2013.01)

(56) References Cited

U.S. PATENT DOCUMENTS

| | | |
|---|---|---|
| 4,763,667 A | 8/1988 | Manzo |
| 5,238,004 A | 8/1993 | Sahatjian et al. |
| 5,299,575 A | 4/1994 | Sandridge |
| 5,318,527 A | 6/1994 | Hyde et al. |
| 5,388,590 A | 2/1995 | Harrigan et al. |
| 5,395,389 A | 3/1995 | Patel |
| 5,549,551 A | 8/1996 | Peacock, III et al. |
| 5,591,194 A * | 1/1997 | Berthiaume ......... A61M 25/00 606/192 |
| 5,658,309 A | 8/1997 | Berthiaume et al. |
| 5,700,269 A | 12/1997 | Pinchuk et al. |
| 5,846,259 A | 12/1998 | Berthiaume |
| 5,961,536 A * | 10/1999 | Mickley ............... A61M 25/10 604/96.01 |
| 5,968,012 A | 10/1999 | Ren et al. |
| 6,099,496 A | 8/2000 | Berthiaume et al. |
| 6,146,415 A | 11/2000 | Fitz |
| 6,200,305 B1 * | 3/2001 | Berthiaume ........ A61M 25/104 604/103.04 |
| 6,270,465 B1 * | 8/2001 | Keith ................ A61M 25/0105 600/585 |
| 6,299,628 B1 | 10/2001 | Harrison et al. |
| 6,443,912 B1 * | 9/2002 | Mazzola ........... A61M 25/0105 600/585 |
| 6,508,803 B1 | 1/2003 | Horikawa et al. |
| 6,527,741 B1 | 3/2003 | Lee et al. |
| 6,582,459 B1 | 6/2003 | Lau et al. |
| 6,592,581 B2 | 7/2003 | Bowe |
| 6,695,863 B1 | 2/2004 | Ramzipoor et al. |
| 6,706,018 B2 | 3/2004 | Westlund et al. |
| 6,884,257 B1 | 4/2005 | Cox |
| 6,911,036 B2 * | 6/2005 | Douk ............... A61B 17/12022 606/200 |
| 6,994,700 B2 | 2/2006 | Elkins et al. |
| 7,326,236 B2 | 2/2008 | Andreas et al. |
| 7,753,889 B2 | 7/2010 | Rosenberg |
| 8,142,401 B2 | 3/2012 | Rosenberg |
| 8,216,182 B2 | 7/2012 | Saab et al. |
| 8,394,056 B2 * | 3/2013 | Saab ................. A61B 17/8855 604/103.08 |
| 8,444,625 B2 | 5/2013 | Stalker et al. |
| 8,491,568 B2 | 7/2013 | Schertiger et al. |
| 8,585,747 B2 | 11/2013 | Andreas et al. |
| 8,617,232 B2 | 12/2013 | Igaki et al. |
| 9,125,020 B2 | 9/2015 | Farhangnia et al. |
| 9,259,551 B2 | 2/2016 | Schertiger et al. |
| 9,327,101 B2 | 5/2016 | Gianotti et al. |
| 2003/0100916 A1 | 5/2003 | Lee et al. |
| 2003/0199960 A1 | 10/2003 | Paskar |
| 2004/0143240 A1 * | 7/2004 | Armstrong ............ A61M 25/00 604/528 |
| 2005/0004553 A1 * | 1/2005 | Douk ............... A61B 17/12022 604/523 |
| 2005/0027236 A1 * | 2/2005 | Douk ................... A61M 1/008 604/40 |
| 2005/0228458 A1 | 10/2005 | Jafari et al. |
| 2006/0241563 A1 | 10/2006 | Vogel et al. |
| 2007/0073329 A1 | 3/2007 | Hardert |
| 2007/0088323 A1 | 4/2007 | Campbell et al. |
| 2008/0255651 A1 | 10/2008 | Dwork |
| 2010/0094257 A1 | 4/2010 | Stalker et al. |
| 2010/0211049 A1 | 8/2010 | Schertiger et al. |
| 2010/0222766 A1 | 9/2010 | Stalker et al. |
| 2013/0110085 A1 | 5/2013 | Adamson |
| 2013/0237950 A1 | 9/2013 | Gianotti et al. |
| 2013/0253467 A1 | 9/2013 | Gianotti et al. |
| 2014/0005768 A1 | 1/2014 | Thomas et al. |
| 2014/0094773 A1 | 4/2014 | Lampropulos et al. |
| 2014/0188205 A1 | 7/2014 | Andreas et al. |
| 2014/0276585 A1 | 9/2014 | Gianotti |
| 2015/0112313 A1 | 4/2015 | Schertiger |
| 2015/0119922 A1 * | 4/2015 | Kamel ............... A61M 25/104 606/194 |

* cited by examiner

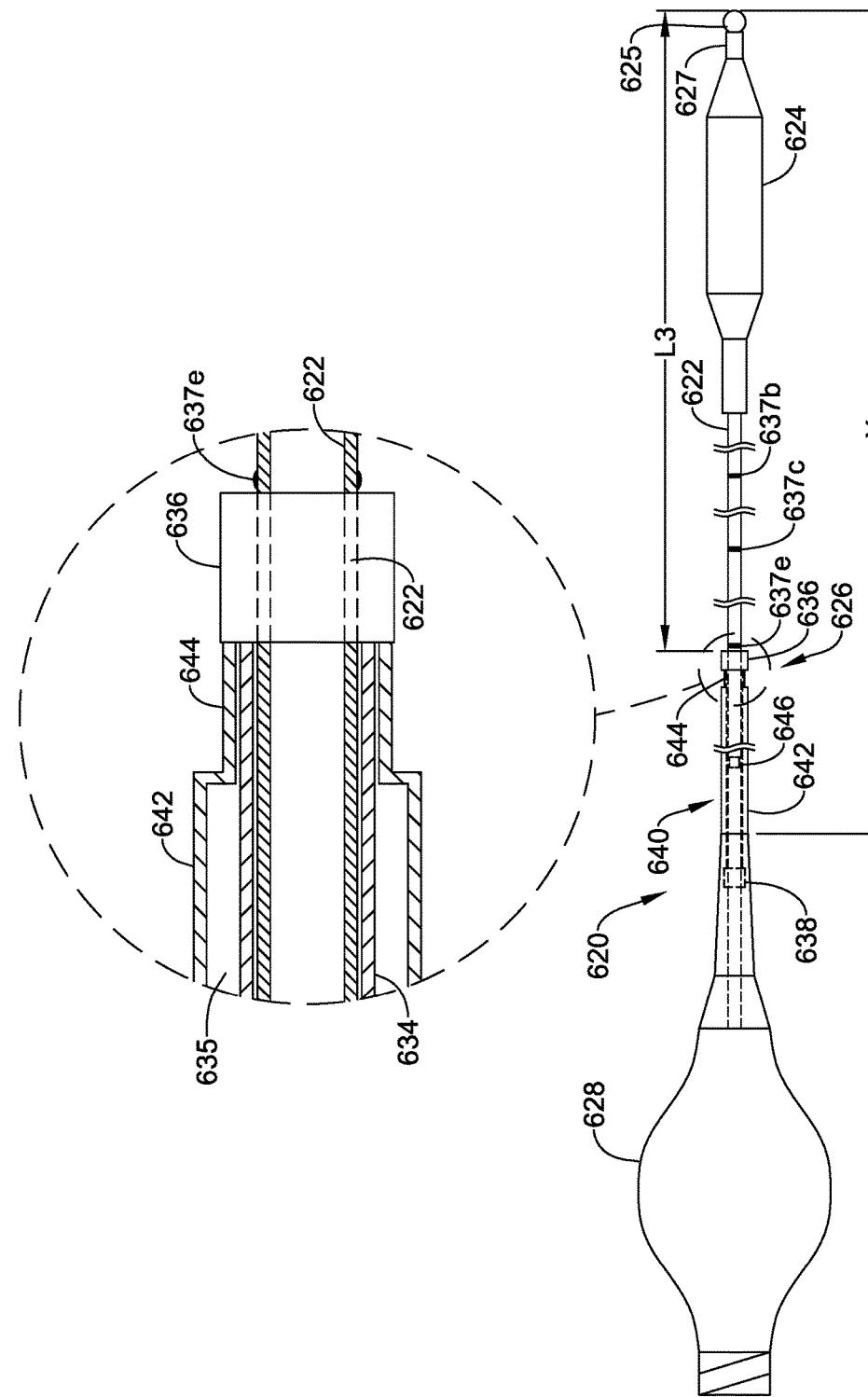

TRAP BALLOON CATHETER WITH TRAP BALLOON RETAINER

CROSS REFERENCE TO RELATED APPLICATIONS

The present application claims the benefit of and priority to U.S. Provisional Patent Application No. 62/279,983, filed Jan. 18, 2016 and to U.S. Provisional Patent Application No. 62/145,496, filed Apr. 9, 2015, the disclosures of which are incorporated herein by reference.

TECHNICAL FIELD

The present disclosure pertains to medical devices, and methods for manufacturing medical devices. More particularly, the present disclosure pertains to trap balloon catheters.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A medical device system is disclosed. The medical device system includes a guide catheter having a proximal end, a distal end, and a lumen extending therebetween. The guide catheter is designed to guide a therapeutic catheter to a target site. The system may also include a guidewire disposed within the lumen of the guide catheter and a trap balloon catheter including a catheter shaft and a balloon coupled to the catheter shaft. The trap balloon catheter is designed to extend through the lumen of the guide catheter to a position adjacent to the distal end of the guide catheter. The balloon is designed to be expanded in order to secure the position of the guidewire relative to the guide catheter by securing the guidewire between the balloon and an inner surface of the guide catheter. The trap balloon catheter includes a trap balloon retainer coupled to the catheter shaft. The trap balloon retainer is designed to prevent a distal end of the trap balloon catheter from extending distally beyond the distal end of the guide catheter.

Alternatively or additionally to any of the embodiments above, the trap balloon retainer includes a slidable member slidably disposed along the catheter shaft and a sheath, the slidable member having a proximal end region disposed within the sheath.

Alternatively or additionally to any of the embodiments above, the slidable to member includes a first stop designed to abut a proximal end region of the guide catheter and a second stop.

Alternatively or additionally to any of the embodiments above, the sheath has a distal end region with a reduced outer diameter, and wherein the second stop is positioned proximally of the distal end region.

Alternatively or additionally to any of the embodiments above, the sheath has a landing region, and wherein the second stop is designed to seat with the landing region.

Alternatively or additionally to any of the embodiments above, the trap balloon retainer includes a tube releasably secured to the catheter shaft.

Alternatively or additionally to any of the embodiments above, the trap balloon retainer includes an axial slit, an axial score line, or both.

Alternatively or additionally to any of the embodiments above, the trap balloon retainer includes a proximal tubular member and a distal tubular member.

Alternatively or additionally to any of the embodiments above, the proximal tubular member abuts the distal tubular member.

Alternatively or additionally to any of the embodiments above, a proximal region of the distal tubular member is disposed within a distal region of the proximal tubular member.

An example method for catheter exchanges is disclosed. The method includes positioning a guide catheter within a body lumen and advancing a guidewire through the guide catheter. A first therapeutic catheter is advanced over the guidewire and through the guide catheter to a target region. A trap balloon catheter is subsequently advanced through the guide catheter. The trap balloon catheter includes a catheter shaft, a balloon coupled to the catheter shaft, and a trap balloon retainer coupled to the catheter shaft. The balloon is inflated to secure the guidewire between the balloon and an inner surface of the guide catheter and then the first therapeutic catheter is retracted from the guide catheter. Thereafter, a second therapeutic catheter is advanced over the guidewire and through the guide catheter.

Alternatively or additionally to any of the embodiments above, further comprising removing the trap balloon retainer from the catheter shaft.

Alternatively or additionally to any of the embodiments above, the trap balloon to retainer includes a tubular member releasably secured to the catheter shaft.

Alternatively or additionally to any of the embodiments above, the trap balloon retainer includes a slidable member slidably disposed along the catheter shaft and a sheath, the slidable member having a proximal end region disposed within the sheath.

Alternatively or additionally to any of the embodiments above, further comprising sliding the slidable member along the catheter shaft to adjust the length of the catheter shaft extending through the guide catheter.

Alternatively or additionally to any of the embodiments above, the slidable member includes a first stop and a second stop, wherein the first stop is positioned distal of the sheath and the second stop is positioned within the sheath.

Alternatively or additionally to any of the embodiments above, the sheath has a distal end region with a reduced outer diameter, and wherein the sheath has a landing region disposed proximally of the distal end region.

Alternatively or additionally to any of the embodiments above, sliding the slidable member along the catheter shaft to adjust the length of the catheter shaft extending through the guide catheter includes sliding the first stop to a position adjacent to adjacent to the distal end region of the sheath.

Alternatively or additionally to any of the embodiments above, sliding the slidable member along the catheter shaft to adjust the length of the catheter shaft extending through the guide catheter includes sliding the second stop to a position adjacent to adjacent to the distal end region of the sheath.

Alternatively or additionally to any of the embodiments above, sliding the slidable member along the catheter shaft to adjust the length of the catheter shaft extending through the guide catheter includes sliding the second stop to the landing region of the sheath.

An example trap balloon catheter is disclosed. The trap balloon catheter includes a catheter shaft extending distally from a hub of the catheter to a distal tip of the catheter. The catheter shaft has an overall length measured from the hub to the distal tip. A trap balloon is attached to a distal end region of the catheter shaft. The trap balloon is designed to be expanded within a guide catheter to secure a guidewire between the trap balloon and an inner surface of the guide catheter. A trap balloon retainer is coupled to the catheter shaft. The trap balloon retainer includes a slidable member slidably disposed along the catheter shaft between a first position providing the catheter with a first working length and a second position providing the catheter with a second working length greater than the first working length. The first working length is compatible with a is first guide catheter length such that the trap balloon is prevented from being positioned distal of a distal end of the guide catheter when the catheter shaft is fully advanced distally through the guide catheter up to the first working length. The second working length is compatible with a second guide catheter length such that the trap balloon is prevented from being positioned distal of the distal end of the guide catheter when the catheter shaft is fully advanced distally through the guide catheter up to the second working length. The overall length of the catheter shaft when the slidable member is at the first position is the same as the overall length of the catheter shaft when the slidable member is at the second position.

Alternatively or additionally to any of the embodiments above, further comprising a sheath surrounding a portion of the catheter shaft, wherein a proximal portion of the slidable member is slidably disposed within the sheath.

Alternatively or additionally to any of the embodiments above, further comprising a first stop located on a proximal end region of the slidable member and a second stop located on a distal end region of the slidable member, wherein the first stop is positioned distal of the sheath and the second stop is positioned within the sheath.

Alternatively or additionally to any of the embodiments above, the sheath has a distal end region with a reduced outer diameter, and the sheath has a landing region disposed proximally of the distal end region.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 15 is a side view of the example trap balloon catheter of FIG. 11 having a third working length.

Figure 1:
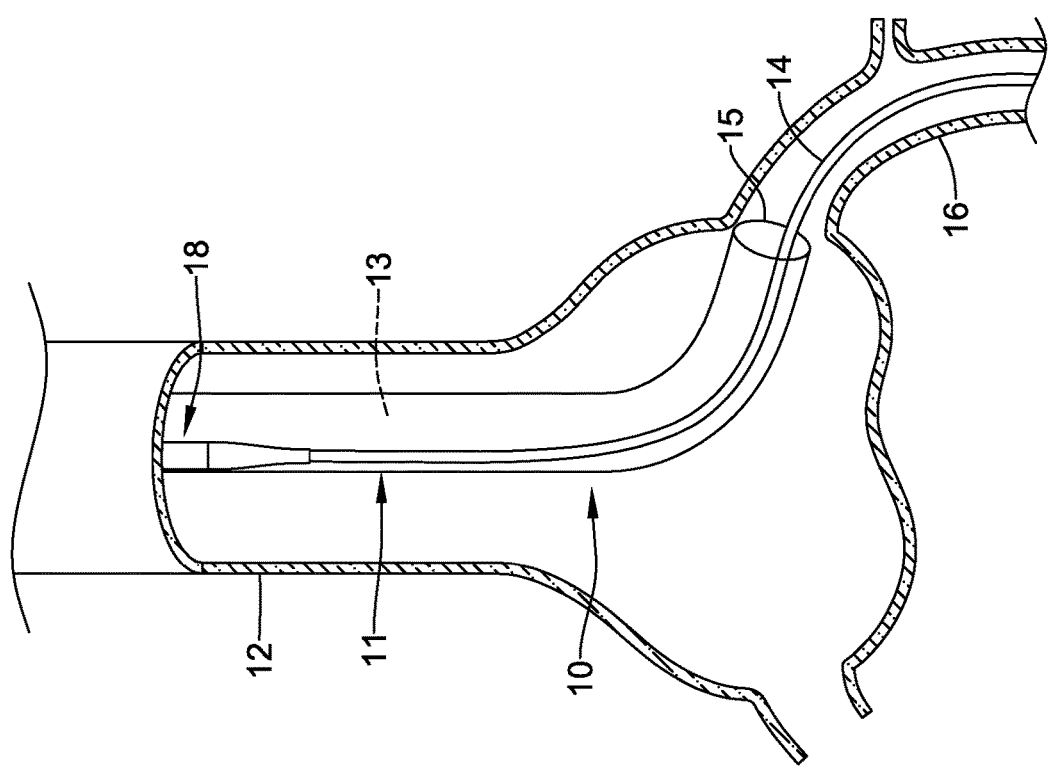
FIG. 1 is a plan view of an example medical device system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of minimally invasive intravascular procedures have been developed. Some of these procedures includes balloon angioplasty and/or the delivery of intravascular stents. At least some of these procedures utilize a guide catheter to help "guide" a therapeutic device to a target. The use of a guide catheter may include advancing the guide catheter through a body lumen (e.g., blood vessel) to a position near a target, advancing a guidewire through the guide catheter, and advancing the therapeutic catheter over the guidewire toward the target. In some instances, it may be desirable to remove the therapeutic catheter and then advance a different therapeutic catheter toward the target. For a number of reasons it may be desirable to maintain the position of the guidewire (which may be desirably positioned relative to the target) during the catheter exchange.

The devices and method disclosed herein are aimed at help to facilitate catheter exchanges. For example, the devices and methods disclosed herein may be designed to help maintain the position of a guidewire during a catheter exchange. Furthermore, the devices and methods disclosed herein may utilize a "retainer" and/or "retainer mechanism" that may allow the devices disclosed herein to be used with differently sized guide catheters. Some of the details regarding these devices and methods are disclosed herein.

FIG. 1 illustrates an example medical device system 10. System 10 may include a number of different components. For example, system 10 may include a guide catheter 11 and a treatment catheter 18 extendable through guide catheter 11. Guide catheter 11 may resemble typical guide catheters. For example, guide catheter 11 may include a catheter shaft having a proximal end (not shown), a distal end 15, and defining a lumen 13 extending at least partially therebetween. A hub assembly (not shown) may be disposed at the proximal end. In use, guide catheter 11 may be advanced through a body lumen or blood vessel 12. In this example, guide catheter 11 is shown disposed within the aorta 12. Other blood vessels and/or body lumens are contemplated. A guidewire 14 may be advanced through or otherwise disposed within lumen 13 of guide catheter 11. Guidewire 14 may extend through the aorta 12 and into a target region 16. In this example, target region 16 is a coronary artery. Other target regions are contemplated.

Figure 2:
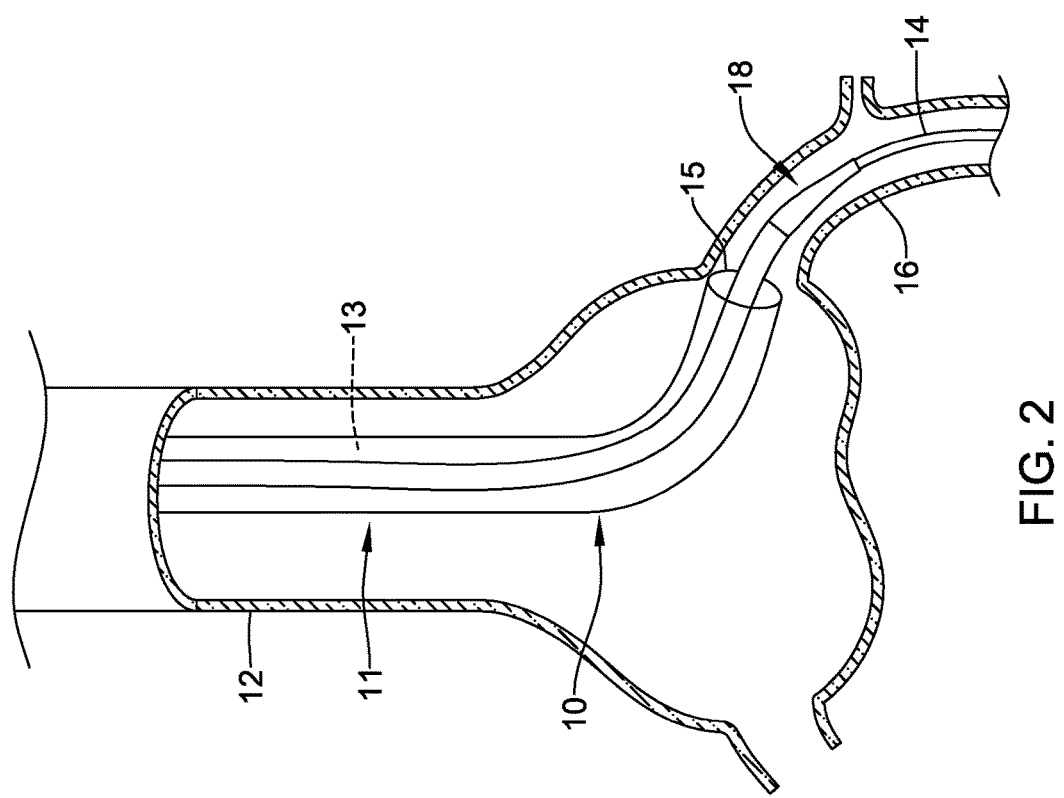
FIG. 2 is a plan view of an example medical device system.

Treatment catheter 18 may extend through guide catheter 11 (e.g., through lumen 13 formed in guide catheter 11) to a position adjacent to or within target region 16 as shown in FIG. 2. This may include advancing treatment catheter 18 over guidewire 14. Treatment catheter 18 may take a variety of different forms. For example, treatment catheter 18 may take the form of a balloon catheter, a stent delivery system, or the like. Treatment catheter 18 may be used for its intended purpose. For example, if treatment catheter 18 is a stent delivery system, treatment catheter 18 may be used to deliver a stent.

Figure 3:
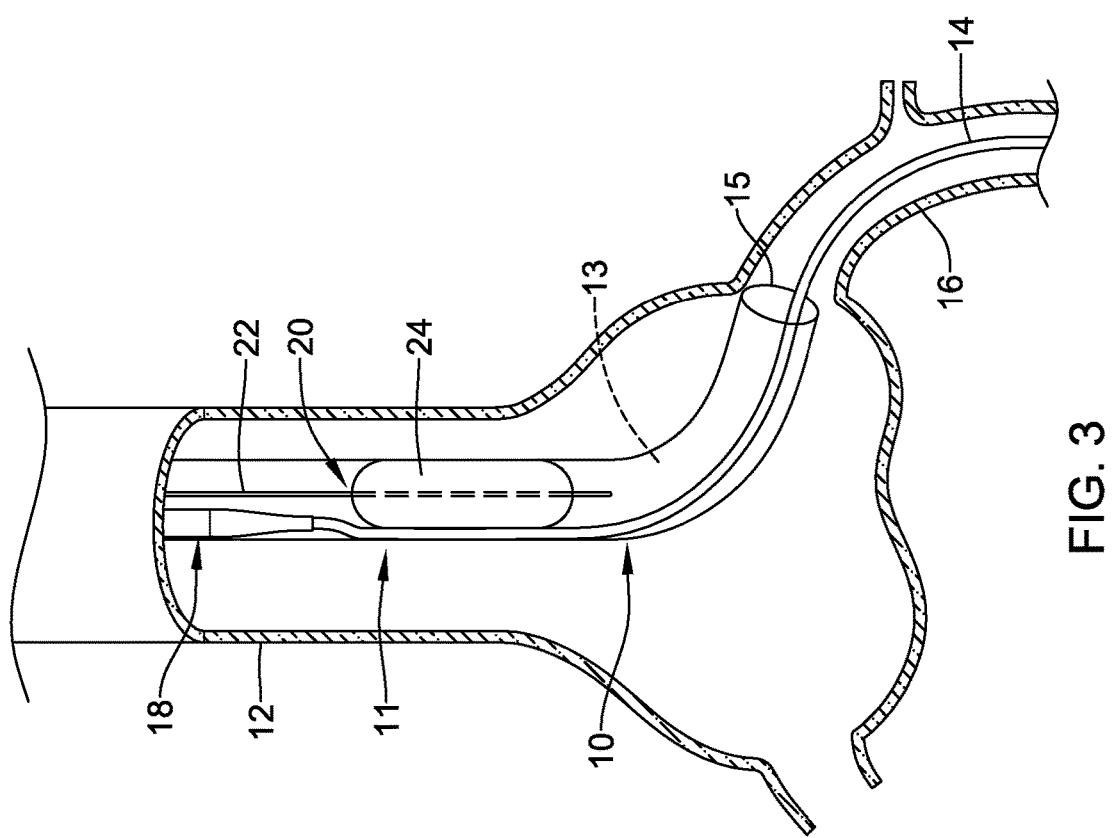
FIG. 3 is a plan view of an example medical device system.

In some instances, it may be desirable to remove treatment catheter 18 and advance a new or different treatment catheter (e.g., a second treatment catheter) over guidewire 14. During the removal of treatment catheter 18 (i.e., first treatment catheter) and/or the advancement of another treatment catheter (e.g., a second treatment catheter), it may be desirable to secure the position of guidewire 14. In order to help secure the position of guidewire 14, a trap balloon catheter 20 may be advanced through lumen 13 of guide catheter 11 as shown in FIG. 3 with guidewire 14 exterior of trap balloon catheter 20.

Figure 4:
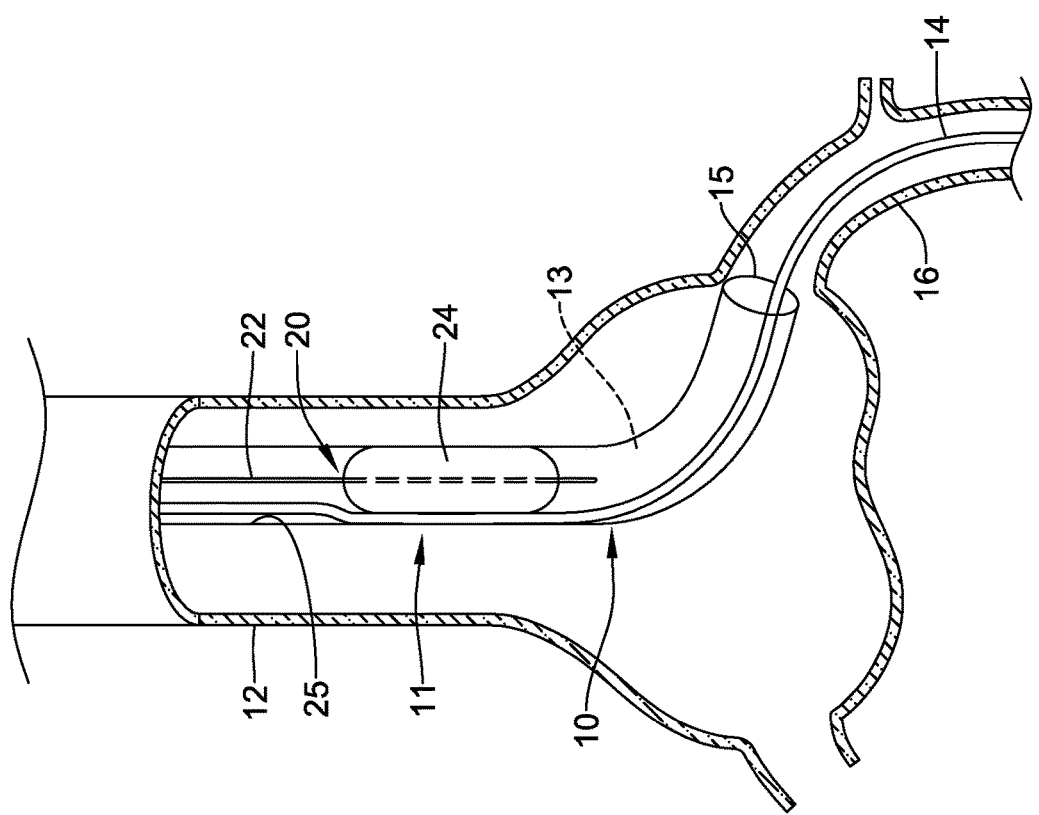
FIG. 4 is a plan view of an example medical device system.

Trap balloon catheter 20 may include a catheter shaft 22 and a balloon 24. Trap balloon catheter 20 may be advanced through lumen 13 of guide catheter 11 while or after treatment catheter 18 is at least partially retracted so that balloon 24 may be positioned distally of the distal end of treatment catheter 18. This may allow trap balloon catheter 20 to be properly positioned so that trap balloon catheter 20 can effectively trap guidewire 14 within lumen 13 of guide catheter 11 while also allowing treatment catheter 18 to still be removed. When suitably positioned, balloon 24 may be expanded to trap guidewire 14 between balloon 24 and an inner surface 25 of lumen 13 of guide catheter 11 as shown in FIG. 4.

When using a trap balloon catheter, such as trap balloon catheter 20, it may be desirable keep balloon 24 from extending beyond the distal end 15 of guide catheter 11. One potential way to keep balloon 24 from extending beyond the distal end 15 of guide catheter 11 is to size trap balloon catheter 20 so that it is "compatible" with a desired guide catheter, such as guide catheter 11. In other words, when using trap balloon catheter 20 with a 90 cm guide catheter 11, catheter shaft 22 may have a length that is sized so that balloon 24 is substantially prevented from extending beyond the distal end of guide catheter 11 (e.g., catheter shaft 22 may have a working length extendable through guide catheter 11 that is less than 90 cm). In some instances, the hub assembly (e.g., which may be disposed at the proximal end of trap balloon catheter 20) may function as a physical barrier that is sufficiently enlarged relative to the lumen of guide catheter 11 so as to prevent trap balloon catheter 20 from advancing too far within guide catheter 11.

It can be appreciated that if sizing, alone, is relied upon for ensuring compatibility of trap balloon catheter 20 with guide catheter 11, a number of differently sized trap balloon catheters 20 may be separately provided for use with each of the differently sized guide catheters. While effective, it may be desirable to have a single sized trap balloon catheter 20 that is compatible with a number of differently sized guide catheters.

Figure 5:
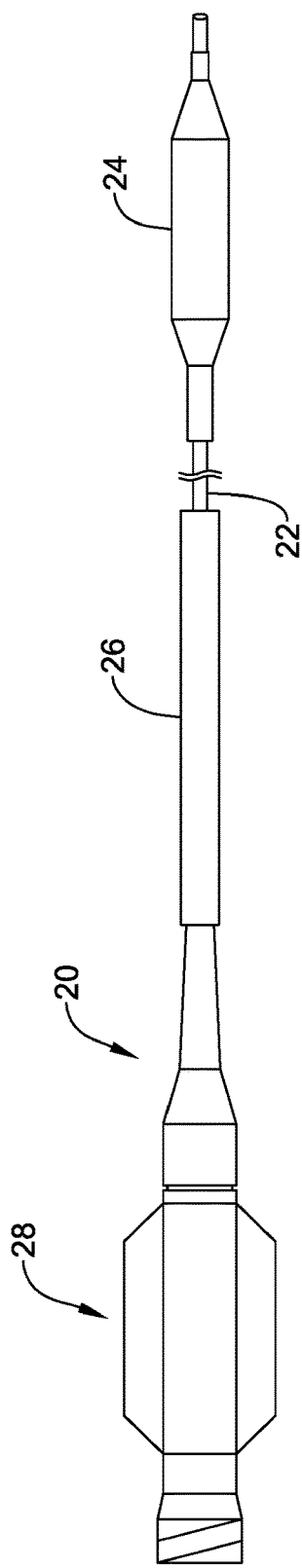
FIG. 5 is a side view of an example trap balloon catheter.

FIG. 5 illustrates trap balloon catheter 20. As indicated above, trap balloon catheter 20 includes catheter shaft 22 and balloon 24. A hub assembly 28 may be coupled to catheter shaft 22. Trap balloon catheter 20 includes a trap balloon retainer 26. Trap balloon retainer 26 is designed to allow trap balloon catheter 20 to be compatible with differently sized guide catheters. For example, trap balloon retainer 26 may be positioned is along catheter shaft 22 and may function as a physical barrier that is designed to keep balloon 24 from extending beyond the distal end of a guide catheter (e.g., guide catheter 11). For example, the diameter of trap balloon retainer 26 may be larger than the inner diameter and/or outer diameter of the guide catheter. In other instances, trap balloon retainer 26 need only be larger than the inner diameter of guide catheter minus the other products expected to be in the guide catheter (e.g., the guidewire being trapped).

In some instances, trap balloon catheter 20 may take the form of a fixed wire catheter. A fixed wire catheter may provide enhanced kink resistance. In other instances, trap balloon catheter 20 may be an over-the-wire catheter that includes a guidewire lumen. In still other instances, trap balloon catheter 20 may be a single-operator-exchange catheter with a shortened guidewire lumen.

Retainer 26 may be releasably coupled to catheter shaft 22. When retainer 26 is disposed along catheter shaft 22, trap balloon catheter 20 may be compatible with a first guide catheter having a first length (e.g., a "short" guide catheter that may have a length, for example, of about 90 cm). When/if desired, retainer 26 may be removed from catheter shaft 22 to convert trap balloon catheter 20 so that it is compatible with a second guide catheter having a second length that is longer than the first length (e.g., a "long" guide catheter that may have a length, for example, of about 100 cm).

In some instances, retainer 26 may be a component that is packaged along with trap balloon catheter 20 in either an attached configuration (e.g., where retainer 26 is positioned along catheter shaft 22) or an unattached configuration (e.g., where retainer 26 is contained within a package along with or otherwise provided with trap balloon catheter 20). Retainer 26 may be labeled with a compatibly message (e.g., "compatible with a 90 cm guide catheter, remove for use with a 100 cm guide catheter" or the like), color coded, noted in the instructions for use, and/or otherwise bear a signal or message that communicates compatibility.

Figure 6:
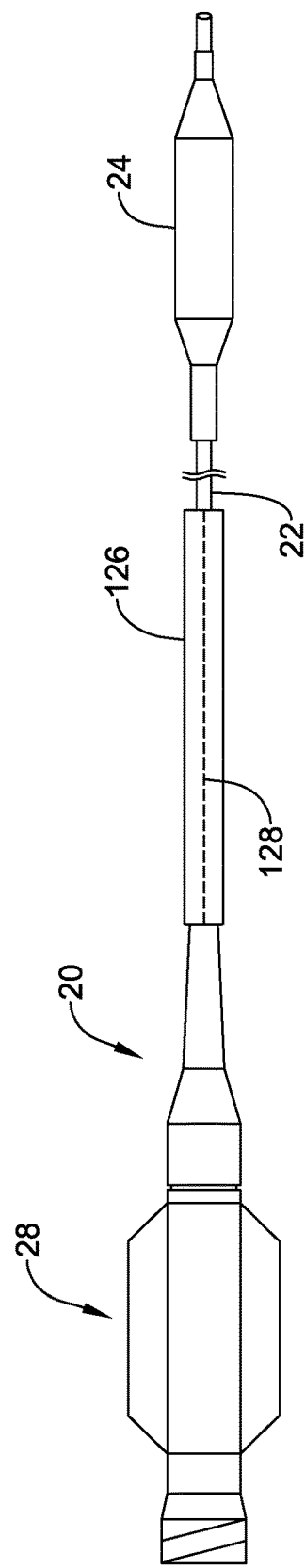
FIG. 6 is a side view of an example trap balloon catheter.

FIG. 6 illustrates an example trap balloon retainer 126, similar in form and function to trap balloon retainer 26 disclosed herein. In this example, retainer 126 includes an axial score line 128. Score line 128 may allow for retainer 126 to be more easily split to as to facilitate removal. In some instances, retainer 126 may include a single slot score is line 128, such as an axial score line. In other instances, retainer 126 may include a plurality of score lines 128. In still other instances, retainer 126 may include a structural feature such as a tab or handle (not shown) that allows retainer 126 to be peeled away from catheter shaft 22.

Figure 7:
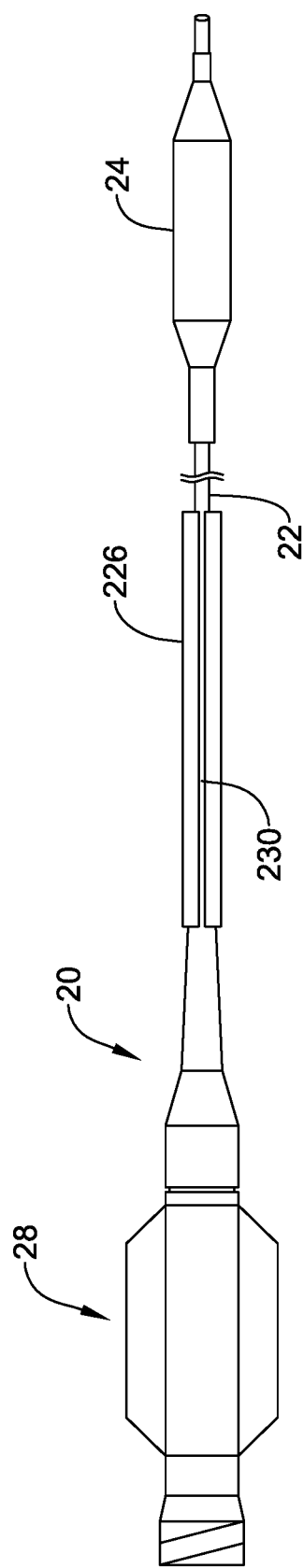
FIG. 7 is a side view of an example trap balloon catheter.

FIG. 7 illustrates an example trap balloon retainer 226, similar in form and function to trap balloon retainer 26 disclosed herein. In this example, retainer 226 includes a slot 230, such as an axial slot. Just like score line 128, slot 230 may allow retainer 226 to be more easily removed from catheter shaft 22. In some instances, retainer 226 may include a single slot 230. In other instances, retainer 226 may include a plurality of slots 230.

Figure 8:
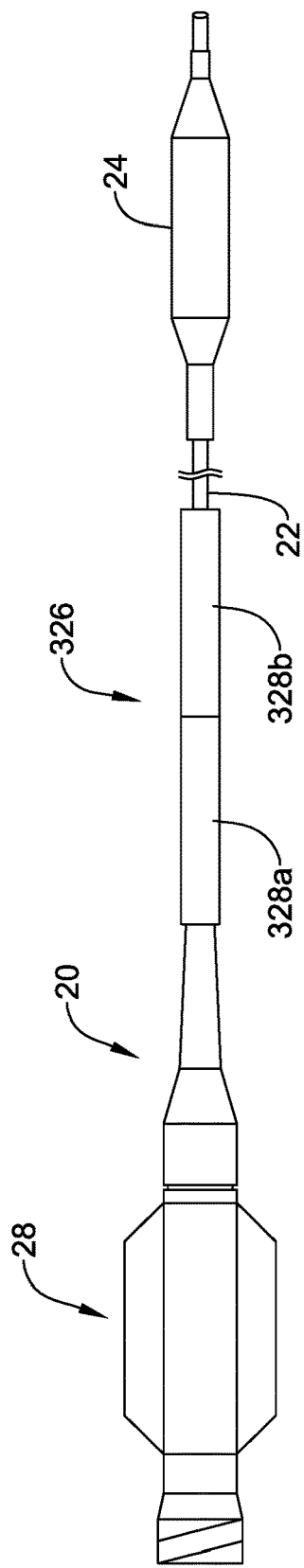
FIG. 8 is a side view of an example trap balloon catheter.

FIG. 8 illustrates an example trap balloon retainer 326, similar in form and function to trap balloon retainer 26 disclosed herein. In this example, retainer 326 includes a first tubular member 328a and a second tubular member 328b. Other retainers are also contemplated that include additional tubular members. The use of multiple tubular members may increase the compatibility of retainer 326 with even more guide catheters. For example, having both tubular members 328a/328b attached to catheter shaft 22 may provide compatibility with a first guide catheter. Removing one tubular member (e.g., second tubular member 328b) may provide compatibility with a second (e.g., longer) guide catheter. Removing both first and second tubular members 328a/328b may provide compatibility with a third (e.g., longer yet) guide catheter. In some instances, first and second tubular members 328a/328b may be color coded in order to more clearly communicate compatibility to a user.

Figure 9:
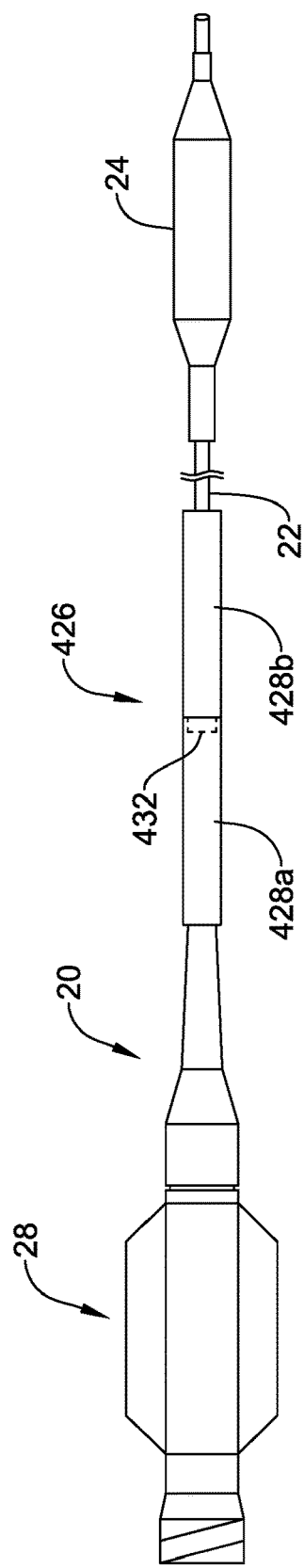
FIG. 9 is a side view of an example trap balloon catheter.

FIG. 9 illustrates an example trap balloon retainer 426, similar in form and function to trap balloon retainer 26 disclosed herein. In this example, retainer 426 includes a first tubular member 428a and a second tubular member 428b. Other retainers are also contemplated that include additional tubular members. Second tubular member 428b may include a necked down region 432 that is designed to be positioned within first tubular member 428b. Alternatively, first tubular member 428a may include necked down region 432 to be positioned within second tubular member 428b. Similar to retainer 326, the use of multiple tubes may enhance the compatibility of retainer 426 with differently sized guide catheters.

Figure 10:
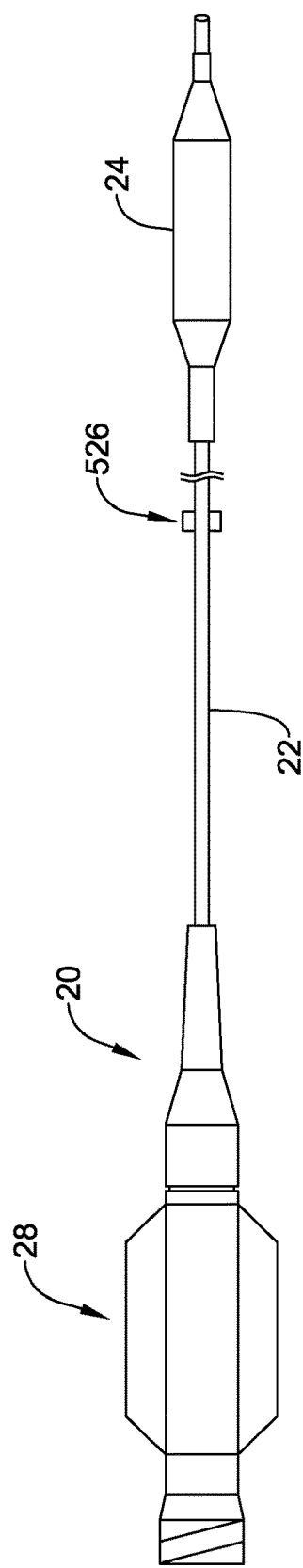
FIG. 10 is a side view of an example trap balloon catheter.

FIG. 10 illustrates an example trap balloon retainer 526, similar in form and function to trap balloon retainer 26 disclosed herein. In this example, retainer 526 is in the form of a clamp. Clamp 526, which is shown schematically, may vary in form. For example, clamp 526 may take the form of a c-clamp. Other forms are contemplated. In some instances, clamp 526 may be disposed at a first position along catheter shaft 22 so as to provide compatibility with a first guide catheter. The first position may be marked or labeled with a suitable marking. Clamp 526 may be movable to a second position along catheter shaft 22 so as to provide compatibility with a second guide catheter. The second position may also be marked or labeled with a suitable marking.

Figure 11:
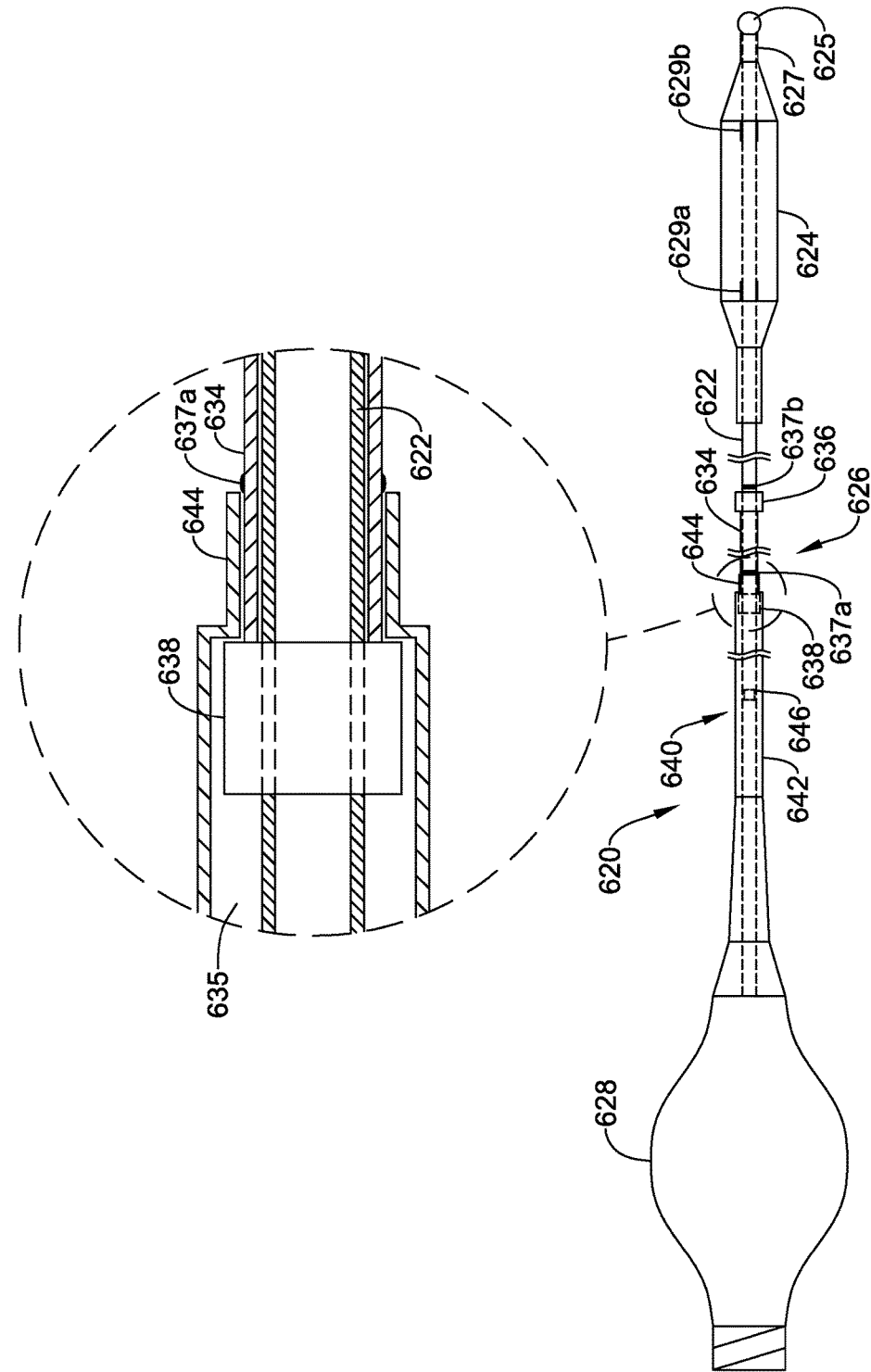
FIG. 11 is a side view of an example trap balloon catheter.

FIG. 11 illustrates an example trap balloon catheter 620 that may be similar in form and function to other trap balloon catheters disclosed herein. Trap balloon catheter 620 includes catheter shaft 622 and balloon 624 coupled to a distal end region of catheter shaft 622 (e.g., adjacent to a distal end of catheter shaft 622). Hub 628 may be coupled to catheter shaft 622 (e.g., attached adjacent to a proximal end of catheter shaft 622). Thus, catheter shaft 622 may be secured to hub 628 and extend distally therefrom to a distal tip of catheter shaft 622.

The form, configuration, and/or sizing of the components of trap balloon catheter 620 may vary. For example, in some instances balloon 624 may have a diameter of about 1 mm to about 4 mm or about 2 mm to about 3 mm, for example. In some instances, the diameter of balloon 624 may be about 2.4 mm +/−0.1 mm or about 2.5 mm +/−0.2 mm. In general, balloon 624 may be sized so that trap balloon catheter 620 may be used with a full range of differently sized guide catheters (e.g., 6F-8F guide catheters). In addition, balloon 624 may be a relatively high pressure balloon. In other words, balloon 624 may be designed to withstand relatively high inflation pressures. For example, balloon 624 may be inflated to a pressure of about 10-14 atm (e.g., 12 atm) and may have a rated burst pressure of about 18-22 atm (e.g., about 20 atm).

In some instances trap balloon catheter 620 may include rounded tip 625 (e.g., as shown in FIGS. 11 and 13-15). Rounded tip 625 may take the form of a metal ball formed as a ball weld at the distal end of trap balloon catheter 620 (e.g., on a distal end of a wire 627). Rounded tip 625 may have a diameter greater than or equal to about 0.019 inches (0.048 cm) or a diameter on the order of about 0.018-0.026 inches (0.046-0.066 cm). In some instances, wire 627 may have a diameter of about 0.012 inches (0.0305 cm). Wire 627 may also include about 10 mm or so of a more flexible proximal section having a diameter of about 0.008 inches (0.020 cm). These sizes may be compatible with a variety of guide catheters (e.g., 6F-8F guide catheters) and may help to reduce the possibility of the distal end of trap balloon catheter 620 (e.g., adjacent rounded tip 625) catching, perforating a vessel, or damaging another interventional device positioned within the guide catheter during a trapping procedure or during device exchanges.

Trap balloon catheter 620 may include one or more radiopaque markers. For example, trap balloon catheter 620 may include a first radiopaque marker 629a, a second radiopaque marker 629b, or both. Markers 629a/629b may be disposed within balloon 624 along shaft 622. In at least some instances, markers 629a/629b may include radiopaque materials such as, for example, platinum and/or iridium. Other materials may also be utilized. Markers 629a/629b may have a length, thickness, or both that is greater than that of markers typically utilized with other devices such as guide catheters. For example, one or both of markers 629a/629b may have a length on the order of about 2 mm (e.g., which may be about twice as long as markers used with other devices) and may have a thickness of about 0.002 inches (0.005 cm; which may be about twice as thick as markers used with other devices). By increasing the length and/or thickness of markers 629a/629b, the relative opacity may be increased, thereby increasing the ability of clinician to visualize markers 629a/629b, for example when trap balloon catheter 620 is positioned within a guide catheter (which could otherwise "dilute" the relative radiopacity of trap balloon catheter 620). Furthermore, the increased length and/or thickness may also help a clinician to better differentiate trap balloon catheter 620 from other radiopaque structures including shorter and/or thinner markers, braids or coils, or the like. In an example, radiopaque markers 629a/629b may be the same or different size.

Just like the other trap balloon catheters disclosed herein, trap balloon catheter 620 is designed to be compatible with guide catheters of differing lengths. For example, trap balloon catheter 620 includes trap balloon retainer 626 that is designed to allow for the working length of catheter shaft 622 that extends into a guide catheter to be adjusted so that balloon 624 can be prevented from extending distally beyond the distal end of the is guide catheter and so that trap balloon catheter 620 can be used with guide catheters of differing lengths. In other words, trap balloon catheter 620 includes a trap balloon retainer 626 that may be actuated by the user between one of a plurality of discrete positions to adjust the working length of trap balloon catheter 620 between one of a plurality of different working lengths. Thus, the maximum distance trap balloon catheter 620 can extend into a guide catheter 11, shown in FIG. 12, (e.g., the maximum distance trap balloon catheter 620 can extend through the lumen of guide catheter 11 from the proximal hub of guide catheter 11) may be adjusted based on the length of guide catheter 11 such that balloon 624 may be maintained within the lumen of guide catheter 11 when trap balloon catheter 620 is fully inserted into guide catheter 11 (e.g., when advanced into lumen of guide catheter 11 up to the full working length).

Retainer 626 may include a slidable member 634 and, in some instances, a sheath 640. Slidable member 634 may be configured to longitudinally slide relative to catheter shaft 622 and/or hub 628 between a plurality of discrete positions, such as first, second and third positions, as described further below. In some instances, slidable member 634 is a telescoping tube surrounding catheter shaft 622 and longitudinally slidable thereover. Slidable member 634 may include one or more stops, such as a first stop 636 and a second stop 638. First stop 636 may be located at distal end of slidable member 634. In some instances, first stop 636 may be secured to distal end of slidable member 634, or first stop 636 may be formed as a unitary portion of slidable member 634. First stop 636 may be designed to abut a proximal end of a guide catheter (e.g., the hub of the guide catheter) and prevent trap balloon catheter 620 from extending any further distally into the lumen of the guide catheter. In other words, first stop 636 may be a physical barrier that stops or limits the working length of catheter shaft 622 that extends into the lumen of the guide catheter while the overall length of the trap balloon catheter 620 (i.e., the length from the hub 628 to the distal tip of catheter shaft 622) is fixed regardless of the position of first and second stops 636/638 and/or slidable member 634. Trap balloon catheter 620 can be adjusted by sliding slidable member 634 along catheter shaft 622. For example, slidable member 634 may be adjusted to or otherwise disposed in a first position that is compatible for use with a first guide catheter having a first length and adjusted to a second position that is compatible for use with a second guide catheter having a second length, different than the first length (e.g., the second length may be greater than the first length). Thus, sliding slidable member 634 to one of a plurality of longitudinal positions allows for trap balloon catheter 620 to be used with guide catheters having different lengths, while keeping balloon 624 from extending distally beyond the distal end of the guide catheter when the trap balloon catheter 620 is inserted into the lumen of the guide catheter up to the full working length of the trap balloon catheter 620.

Sheath 640 may be disposed along catheter shaft 622 and may take the form of a tubular member that is coupled to or fixed relative to hub 628 and extends distally from hub 628 along catheter shaft 622. Sheath 640 may surround catheter shaft 622 to define an annular space 635 between the outer surface of catheter shaft 622 and the inner surface of sheath 640. A proximal end region of slidable member 634, including second stop 638, may extend into sheath 640 through a distal opening of sheath 640, with a distal end region of slidable member 634, including first stop 636 extending distal of sheath 640. Slidable member 634 may longitudinally slide along catheter shaft 622 relative to sheath 640, which may be fixed relative to catheter shaft 622.

Sheath 640 may have a body region 642 and a distal end region 644. In some instances, distal end region 644 may have a reduced outer diameter (e.g., the outer diameter of distal end region 644 may be reduced relative to the outer diameter of body region 642). Additionally or alternatively, the inner diameter of distal end region 644 may be reduced relative to the inner diameter of the body region 642. Sheath 640 may also include a stop, such as a landing region 646, in some instances. Landing region 646 may take the form of a slight reduction in the inner diameter of sheath 640 (e.g., necked down region of sheath 640) that forms a physical barrier for further proximal movement of second stop 638 within sheath 640. In other instances, landing region 646 may have a different configuration, such as one or more protrusions configured to restrict proximal movement of second stop 638 past landing region 646. Thus, second stop 638 may be partially "locked" or otherwise stopped from moving further proximally by contact with landing region 646. However, in at least some instances, a user may apply additional force to slidable member 634 in order to further slide slidable member 634 proximally within sheath 640 such that second stop 638 is moved proximally past landing region 646.

Figure 12:
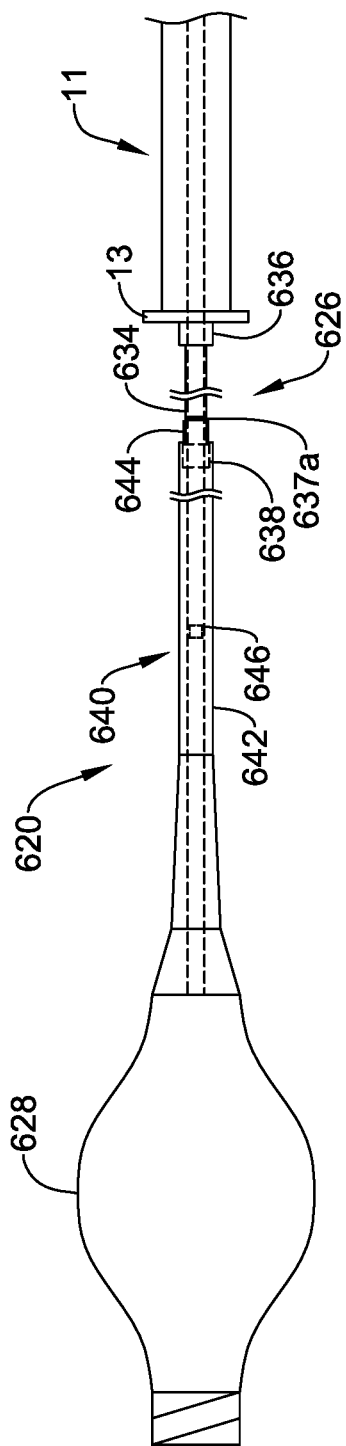
FIG. 12 is a side view of the example trap balloon catheter of FIG. 11 and an example guide catheter.

In use, retainer 626 may be oriented so that second stop 638 (which is located at the proximal end region of slidable member 634, such as secured to or unitarily formed with the slidable member 634) is disposed within sheath 640 and positioned proximally of distal end region 644. In some instances, the size reduction in sheath 640 at distal end region 644 (e.g., of outer diameter, inner diameter, or both) may be less than the outer diameter of second stop 638 to effectively "lock" second stop 638 within sheath 640 and, thus, limit the distal movement of slidable member 634. First stop 636 (which is located at the distal end region of slidable member 634, such as secured to or unitarily formed with the slidable member 634, and positioned exterior to sheath 640) may be positioned distally of distal end region 644. First stop 636 may abut the proximal end and/or hub 13 of guide catheter 11 as shown in FIG. 12 when trap balloon catheter 620 is fully inserted into guide catheter 11. Because of this, the working length of catheter shaft 622 extending into guide catheter 11 corresponds to the length of catheter shaft 622 that is distal of first stop 636. Adjusting the position of slidable member 634 and, thus, the position of first stop 636 along catheter shaft 622 adjusts the working length of catheter shaft 622 permitted to extend into guide catheter 11.

Figure 13:
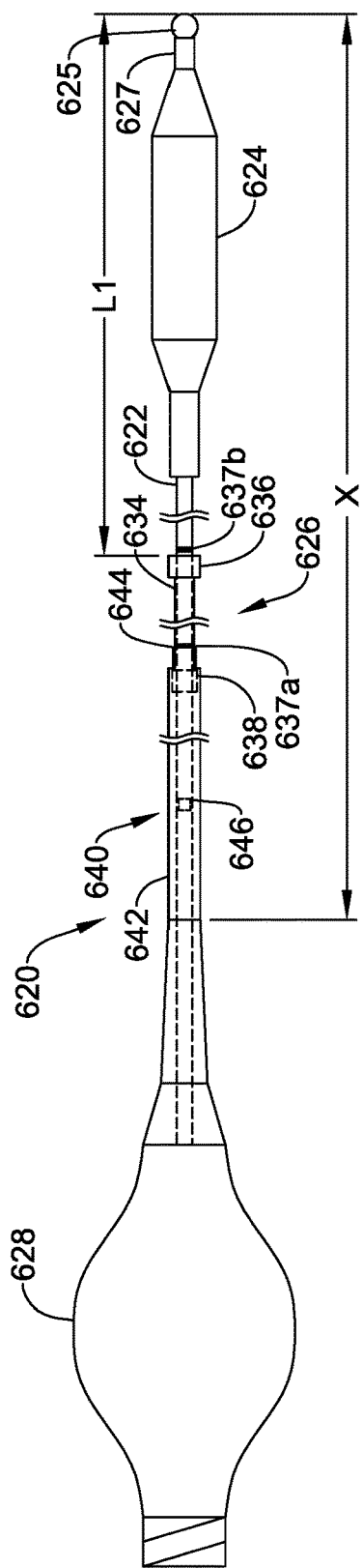
FIG. 13 is a side view of the example trap balloon catheter of FIG. 11 having a first working length.
Figure 14:
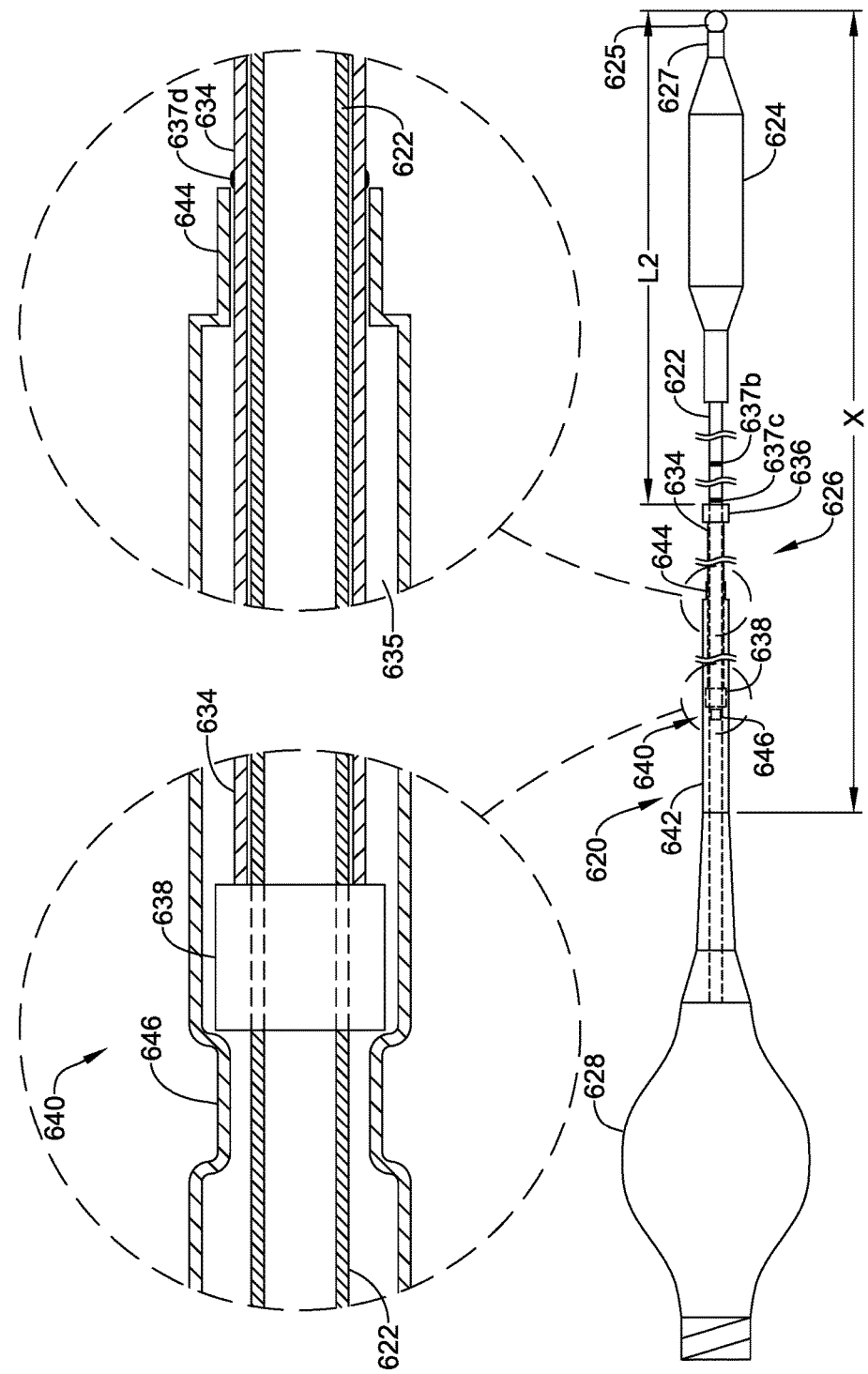
FIG. 14 is a side view of the example trap balloon catheter of FIG. 11 having a second working length.

At least some of the adjustable lengths of catheter shaft 622 (e.g., the length of catheter shaft 622 that can extend into catheter shaft 11 in order to keep balloon 624 from extending beyond the distal end of guide catheter 11) that can be accomplished using retainer 626 are shown in FIGS. 13-15. For example, slidable member 634 may be positioned at a first position where second stop 638 is positioned adjacent to or otherwise abuts distal end region 644 as shown in FIG. 13. The first position may be a position in which slidable member 634 is at its distalmost extent. This defines a first working length L1 of catheter shaft 622 that can extend into guide catheter 11. In some instances, first working length L1 may correspond to the shortest working length of catheter shaft 622 that can extend into guide catheter. Thus, when retainer 626 is oriented as shown in FIG. 13, trap balloon catheter 620 may be compatible with a first guide catheter having a working length (e.g., a 90 cm guide catheter). When slidable member 634 is positioned at the first position (corresponding to use of trap balloon catheter 620 with a guide catheter having a specified working length (e.g., a 90 cm guide catheter)), full working length L1 of trap balloon catheter 620 can be inserted into the lumen of the guide catheter having the specified working length while the balloon 624 remains within the lumen of the guide is catheter and is prevented from extending out the distal end of the guide catheter.

Regardless of the working length (e.g., first working length L1) and/or position of slidable member 634, an overall length X of trap balloon catheter 620 (i.e., the length from hub 628 to the distal tip of catheter shaft 622) remains constant. In some instances, catheter shaft 622 may include a detent and/or retaining mechanism that helps to hold slidable member 634 at the first position.

Slidable member 634 may be slid proximally to a second position such as until second stop 638 is disposed at landing region 646, as shown in FIG. 14. This may include abutting second stop 638 with landing region 646 or positioning second stop 638 within or along landing region 646. Doing so may define a second working length L2 of catheter shaft 622 that can extend into guide catheter 11. The second working length L2 may be greater than the first working length L1. In some instances, second working length L2 may correspond to an intermediate working length of catheter shaft 622 that can extend into guide catheter. Thus, when retainer 626 is oriented as shown in FIG. 14, trap balloon catheter 620 may be compatible with a second guide catheter having a working length greater than the working length of the first guide catheter (e.g., a 100 cm guide catheter). When slidable member 634 is positioned at the second position (corresponding to use of trap balloon catheter 620 with a guide catheter having a specified working length (e.g., a 100 cm guide catheter)), the full working length L2 of trap balloon catheter 620 can be inserted into the lumen of the guide catheter having the specified working length while balloon 624 remains within the lumen of the guide catheter and is prevented from extending out the distal end of the guide catheter. In some instances, catheter shaft 622 may include a detent and/or retaining mechanism that helps to hold slidable member 634 at the second position.

Slidable member 634 may be slid further proximally (e.g., where second stop 638 is disposed proximally of landing region 646) to a third position such as until first stop 636 abuts or nests with distal end region 644, as shown in FIG. 15. This defines a third working length L3 of catheter shaft 622 that can extend into guide catheter 11. The third working length L3 may correspond to the longest working length of catheter shaft 622 that can extend into guide catheter 11. In some instances, catheter shaft 622 may include a detent and/or retaining mechanism that helps to hold slidable member 634 at the third is position.

In some instances, positioning slidable member 634 at the second position, shown in FIG. 14, may position balloon 624 a relatively short distance proximally of the distal end of the guide catheter (e.g., when used with a 100 cm guide catheter). It may be desirable to shift balloon 624 distally within the guide catheter to a position adjacent to the distal end of the guide catheter. Shifting slidable member 634 to the third position (e.g., when retainer 626 is oriented as shown in FIG. 15) may elongate the working length of catheter shaft 622 such that balloon 624 is positioned at the distal end of the guide catheter, yet engagement of first stop 636 with hub of guide catheter 11 prevents the balloon 624 from extending out distal end of guide catheter 11. In some instances, moving slidable member 634 from second position to the third position may elongate the working length of catheter shaft 622 an additional 2-10 cm (e.g., about 5 cm). It can be appreciated that a number of additional lengths/adjustments are contemplated beyond what is shown. For example, sheath 640 may include a number of additional discrete positions such as landing regions that allow for greater length variability.

It is noted that catheter shaft 622 maintains a constant overall length X (i.e., the length measured from the hub 628 to the distal tip of the catheter shaft 622) regardless of which position the slidable member 634 is at. For example, the overall length X of the catheter shaft 622 of catheter 620 when slidable member 634 is positioned at the first position, providing a first working length L1, may be the same as the overall length X of catheter shaft 622 of catheter 620 when slidable member 634 is positioned at the second position, providing a second working length L2, greater than the first working length L1.

Furthermore, the overall length X of catheter shaft 622 of catheter 620 when slidable member 634 is positioned at the second position, providing a second working length L2, may be the same as the overall length X of catheter shaft 622 of catheter 620 when slidable member 634 is positioned at the third position, providing a third working length L3, greater than the second working length L2.

Catheter shaft 622 and/or slidable member 634 may include one or more visual markings that may aid a user in assessing which position/configuration that slidable member 634 is in and, thus, which length of guide catheter that trap balloon catheter 620 may be compatible with to insure balloon 624 is prevented from being positioned distal of the guide catheter when fully inserted into the guide catheter. For example, slidable member 634 may include a visual marker 637*a* positioned distally of second stop 638 that is visible (e.g., exposed or otherwise uncovered by sheath 640) when slidable member 634 is in the first position. In some of these and in other embodiments, catheter shaft 622 may include a visual marker such as a visual marker 637*b*. Visual marker 637*b* may be visible and generally positioned distally of and adjacent to first stop 636 when slidable member 634 is in the first position. In some of these and in other embodiments, slidable member 634 may include a visual marker 637*d* that is positioned distally of second stop 638 that is visible (e.g., exposed or otherwise uncovered by sheath 640) when slidable member 634 is in the second position. In some of these and in other embodiments, catheter shaft 622 may include a visual marker 637*c* that may be visible and generally positioned distally of and adjacent to first stop 636 when slidable member 634 is in the second position. In some of these and in other embodiments, catheter shaft 622 may include a visual marker 637*e* that may be visible and generally positioned distally of and adjacent to first stop 636 when slidable member 634 is in the third position. It can be appreciated that any number and/or combinations of visual markers (e.g., visual markers along slidable member 634, visual markers along catheter shaft 622, or both) may be utilized including those disclosed herein to provide a visual indication and confirmation of which position the slidable member 634 is positioned. The visual marker(s) may insure the correct working length of the trap balloon catheter 620 is set for use with a guide catheter of a specified corresponding working length. Other arrangements are contemplated.

While the adjustable working lengths for trap balloon catheter 620 may be adjusted to be used with 90 cm and 100 cm guide catheters as examples in cardiology, these lengths are not intended to be limiting. The desired trapping position and/or working length for trap balloon catheter 620 may vary. For example, in some instances it may be desirable to configure the working length of trap balloon catheter 620 so that the distal end thereof (and/or balloon 624) is positioned at, adjacent, or just proximal to a distal curve in the guide catheter, which may be about 5 cm or so from the distal end of the guide catheter. In some of these and in other instances it may be desirable to adjust the working length of trap balloon catheter 620 to about 97 cm +/−1 cm (which may be effective for use with a 90 cm guide catheter with a hemostatic valve), to about 107 cm +/−1 cm (which may be effective for use with a 100 cm guide catheter with a hemostatic valve), to about 112 cm +/−1 cm (which may be effective for positioning the distal end of trap balloon catheter 620 adjacent to, but without exiting, the distal end of a 100 cm guide catheter with a hemostatic valve), or other suitable lengths. These are just examples. Other lengths are contemplated.

The materials that can be used for the various components of system 10 (and/or other systems and/or trap balloon catheters and/or retainers disclosed herein) may include those commonly associated with medical devices. For simplicity purposes, the following discussion makes reference to trap balloon catheter 20. However, this is not intended to limit the devices and methods described herein, as the discussion may be applied to other similar tubular members and/or components of tubular members or devices disclosed herein.

Trap balloon catheter 20 and/or other trap balloon catheters disclosed herein may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of trap balloon catheter 20 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of trap balloon catheter 20 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of trap balloon catheter 20 to achieve the same result.

In some embodiments, a degree of Magnetic Resonance Imaging (MRI) compatibility is imparted into trap balloon catheter 20. For example, trap balloon catheter 20, or portions thereof, may be made of a material that does not substantially distort the image and create substantial artifacts (e.g., gaps in the image). Certain ferromagnetic materials, for example, may not be suitable because they may create artifacts in an MRI image. Trap balloon catheter 20, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A trap balloon catheter, comprising:
a catheter shaft extending distally from a hub of the catheter to a distal tip of the catheter, the catheter shaft having an overall length measured from the hub to the distal tip;
a trap balloon attached to a distal end region of the catheter shaft, the trap balloon being designed to be expanded within a guide catheter to secure a guidewire between the trap balloon and an inner surface of the guide catheter;
a trap balloon retainer coupled to the catheter shaft, the trap balloon retainer including a slidable member slidably disposed along the catheter shaft between a first position providing the catheter with a first working length and a second position providing the catheter with a second working length greater than the first working length;
wherein the first working length is configured to prevent the trap balloon from being positioned distal of a distal end of a first guide catheter when the catheter shaft is fully advanced distally through the first guide catheter up to the first working length;
wherein the second working length is configured to prevent the trap balloon from being positioned distal of distal end of a second guide catheter when the catheter shaft is fully advanced distally through the second guide catheter up to the second working length; and
wherein the overall length of the catheter shaft when the slidable member is at the first position is the same as the overall length of the catheter shaft when the slidable member is at the second position.

2. The trap balloon catheter of claim 1, further comprising a sheath surrounding a portion of the catheter shaft, wherein a proximal portion of the slidable member is slidably disposed within the sheath.

3. The trap balloon catheter of claim 2, further comprising a first stop located on a distal end region of the slidable member and a second stop located on a proximal end region of the slidable member, wherein the first stop is positioned distal of the sheath and the second stop is positioned within the sheath.

4. The trap balloon catheter of claim 3, wherein the sheath has a distal end region with a reduced outer diameter, and wherein the sheath has a landing region disposed proximally of the distal end region of the sheath.

5. The trap balloon catheter of claim 4, wherein the second stop is slidable between the distal end region of the sheath and the landing region of the sheath.

6. The trap balloon catheter of claim 5, wherein the sheath has an inner diameter distal of the landing region that is greater than an inner diameter of the landing region.

7. The trap balloon catheter of claim 6, wherein the second stop is configured to engage the landing region when the slidable member is in the second position.

8. The trap balloon catheter of claim 7, wherein the slidable member is a tubular member surrounding the catheter shaft.

9. The trap balloon catheter of claim 7, wherein the second stop is configured to engage the reduced diameter distal end region of the sheath when the slidable member is in the first position.

10. The trap balloon catheter of claim 9, wherein the slidable member is a tubular member surrounding the catheter shaft.

11. The trap balloon catheter of claim 1, wherein the slidable member is slidable to a third position to provide the catheter with a third working length greater than the second working length.

12. The trap balloon catheter of claim 11, wherein the third working length is 2 to 10 cm greater than the second working length.

13. The trap balloon catheter of claim 12, wherein the second working length is 10 cm greater than the first working length.

14. The trap balloon catheter of claim 11, wherein the overall length of the catheter shaft when the slidable member is at the third position is the same as the overall length of the catheter shaft when the slidable member is at the first or second positions.

15. A trap balloon catheter, comprising:
- a catheter shaft extending distally from a hub of the catheter to a distal tip of the catheter, the catheter shaft having an overall length measured from the hub to the distal tip;
- a trap balloon attached to a distal end region of the catheter shaft, the trap balloon being designed to be expanded within a guide catheter to secure a guidewire between the trap balloon and an inner surface of the guide catheter;
- a trap balloon retainer coupled to the catheter shaft, the trap balloon retainer including a tubular member surrounding the catheter shaft;
- a sheath fixed to the catheter shaft and surrounding a proximal end region of the tubular member;
- wherein the tubular member is longitudinally slidable relative to the catheter shaft between a first position and a second position;
- wherein the overall length of the catheter shaft when the tubular member is at the first position is the same as the overall length of the catheter shaft when the tubular member is at the second position.

16. The trap balloon catheter of claim 15, further comprising a first stop located on a distal end region of the tubular member and a second stop located on a proximal end region of the tubular member.

17. The trap balloon catheter of claim 16, wherein the second stop is positioned within the sheath in both the first position and the second position.

18. The trap balloon catheter of claim 17, wherein the first stop is positioned distal of the sheath in both the first position and the second position.

19. The trap balloon catheter of claim 18, wherein the sheath has a distal end region with a reduced outer diameter and a landing region disposed proximally of the distal end region of the sheath, wherein the second stop is slidable between the distal end region of the sheath and the landing region of the sheath.

20. The trap balloon catheter of claim 15, wherein positioning the tubular member at the first position provides the catheter with a first working length and positioning the tubular member at the second position provides the catheter with a second working length greater than the first working length while the overall length remains constant.

* * * * *